(12) United States Patent
Kontos

(10) Patent No.: US 8,715,227 B2
(45) Date of Patent: May 6, 2014

(54) MULTI-STRANDED APPARATUS FOR TREATING A MEDICAL CONDITION

(75) Inventor: Daphne Kontos, Washington, DC (US)

(73) Assignee: Cook Medical Technologies LLC, Bloomington, IN (US)

( * ) Notice: Subject to any disclaimer, the term of this patent is extended or adjusted under 35 U.S.C. 154(b) by 510 days.

(21) Appl. No.: 12/504,148

(22) Filed: Jul. 16, 2009

(65) Prior Publication Data
US 2010/0023035 A1 Jan. 28, 2010

Related U.S. Application Data

(60) Provisional application No. 61/082,712, filed on Jul. 22, 2008.

(51) Int. Cl.
*A61M 29/00* (2006.01)

(52) U.S. Cl.
USPC ........................................ 604/96.01; 606/159

(58) Field of Classification Search
USPC ......... 606/158, 159, 200; 604/22, 96.01, 508; 600/585
See application file for complete search history.

(56) References Cited

U.S. PATENT DOCUMENTS

| | | | |
|---|---|---|---|
| 4,569,347 A | 2/1986 | Frisbie | |
| 4,637,396 A | 1/1987 | Cook | |
| 4,921,484 A | 5/1990 | Hillstead | |
| 4,936,826 A | 6/1990 | Amarasinghe | |
| 5,092,847 A * | 3/1992 | Pozzo | 604/170.02 |
| 5,104,388 A | 4/1992 | Quackenbush | |
| 5,211,654 A | 5/1993 | Kaltenbach | |
| 5,257,974 A | 11/1993 | Cox | |
| 5,695,469 A | 12/1997 | Segal | |
| 5,814,062 A * | 9/1998 | Sepetka et al. | 606/198 |
| 6,080,141 A | 6/2000 | Castro et al. | |
| 6,355,013 B1 | 3/2002 | Van Muiden | |
| 6,416,529 B1 | 7/2002 | Holman et al. | |
| 6,939,327 B2 | 9/2005 | Hall et al. | |
| 2006/0178685 A1 | 8/2006 | Melsheimer | |
| 2006/0229669 A1* | 10/2006 | Mirizzi et al. | 606/213 |
| 2007/0016233 A1* | 1/2007 | Ferrera et al. | 606/159 |

* cited by examiner

*Primary Examiner* — Victor Nguyen
(74) *Attorney, Agent, or Firm* — Brinks Gilson & Lione

(57) ABSTRACT

The present embodiments provide apparatus suitable for treating a medical condition at a target site. In one embodiment, the apparatus has a plurality of strands, each having proximal and distal regions, wherein the plurality of strands are twisted in a generally helical manner to form a tubular shape. The proximal and distal regions of each of the plurality of strands have a contracted configuration adapted for delivery to the target site. Further, the distal region of at least one of the plurality of strands has an expanded, radially deployed configuration adapted to facilitate treatment of the medical condition. The distal region of at least one of the plurality of strands may be deployed in a self-expanding or balloon-expandable manner.

20 Claims, 5 Drawing Sheets

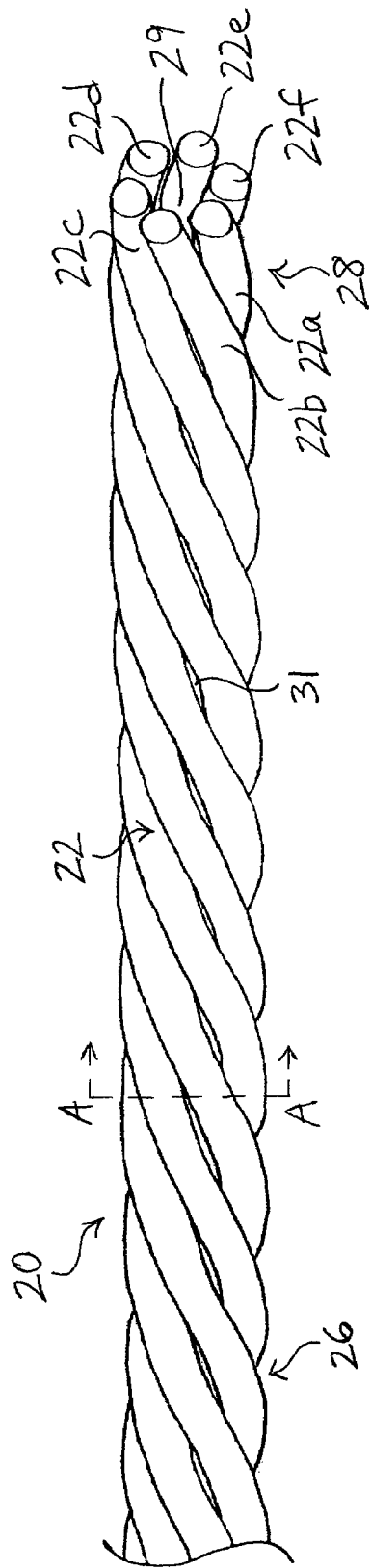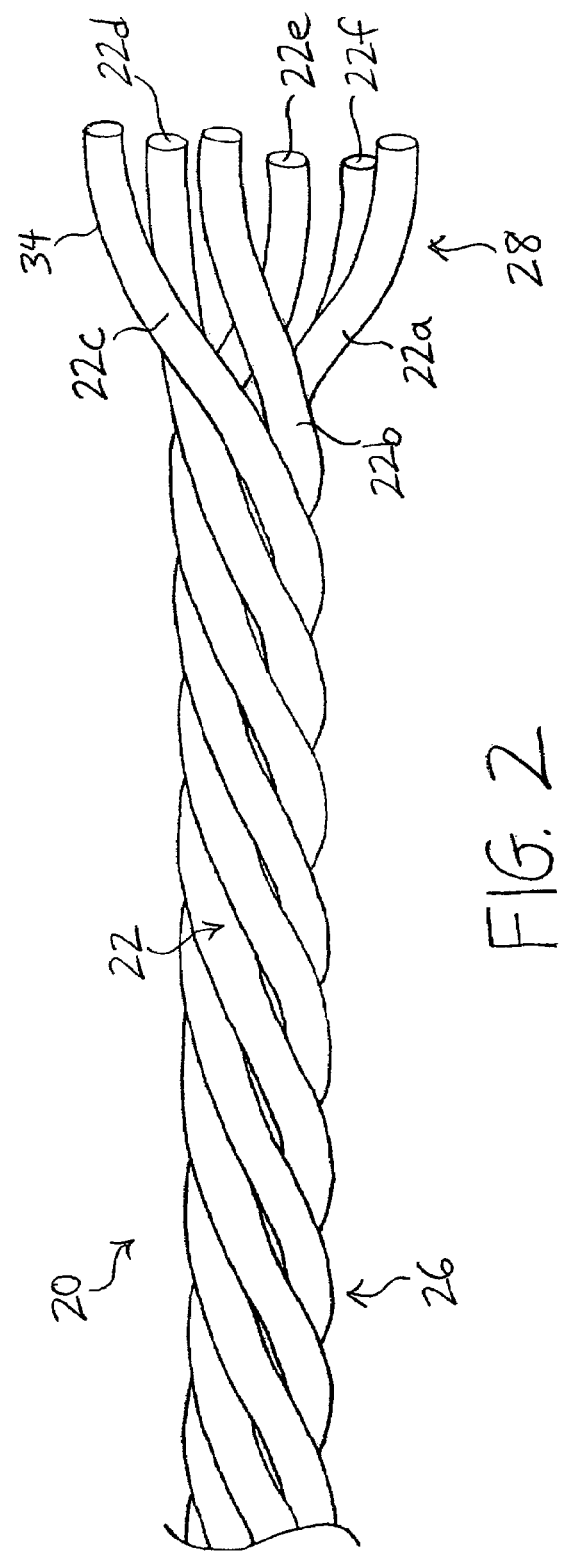

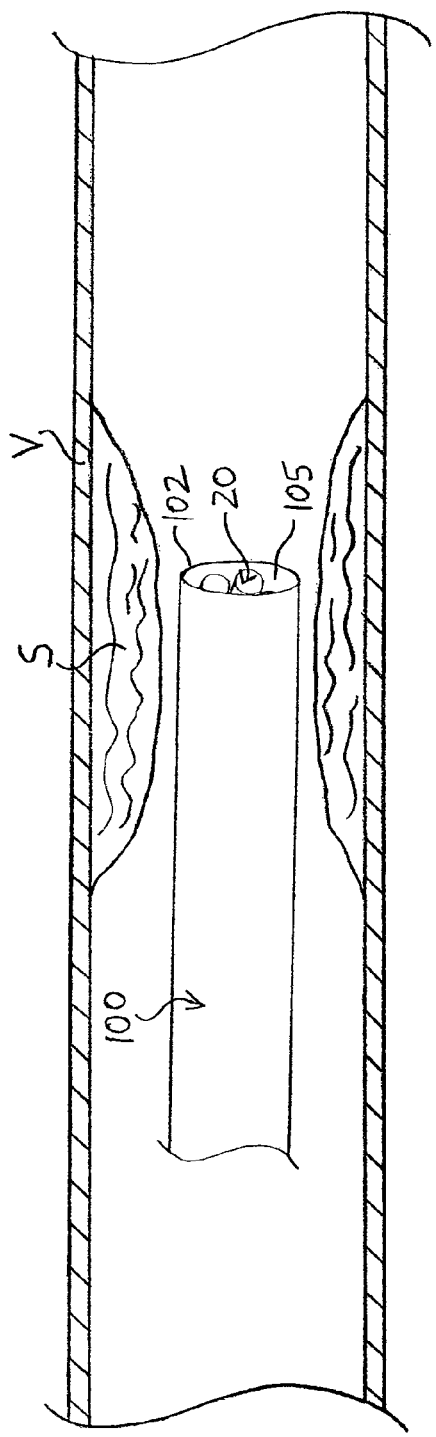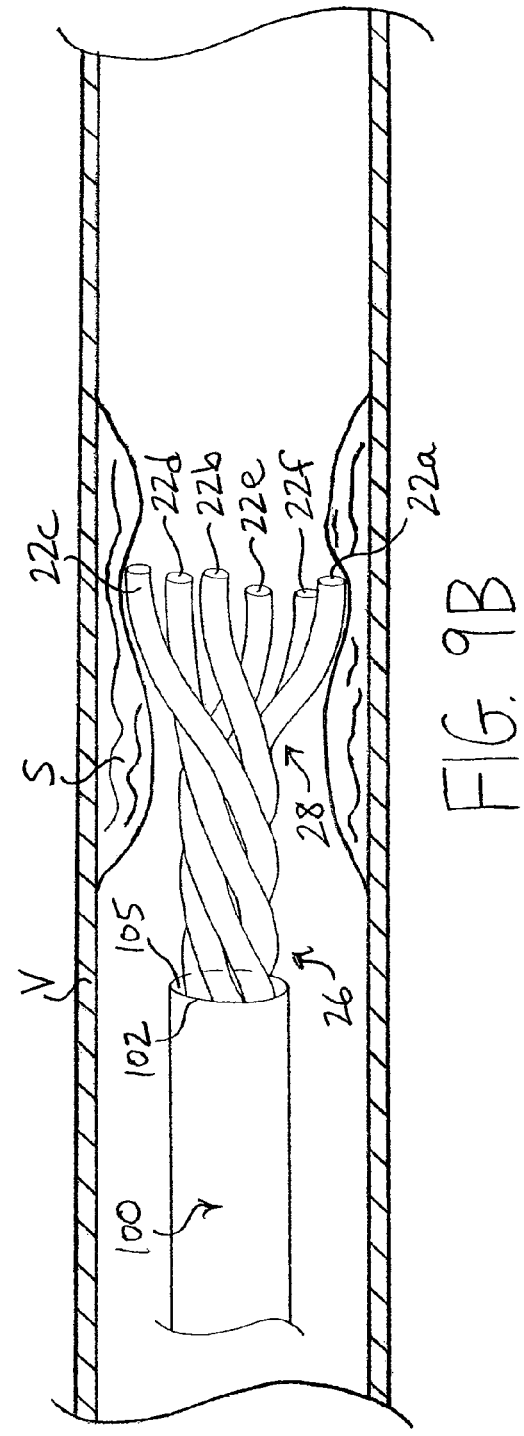

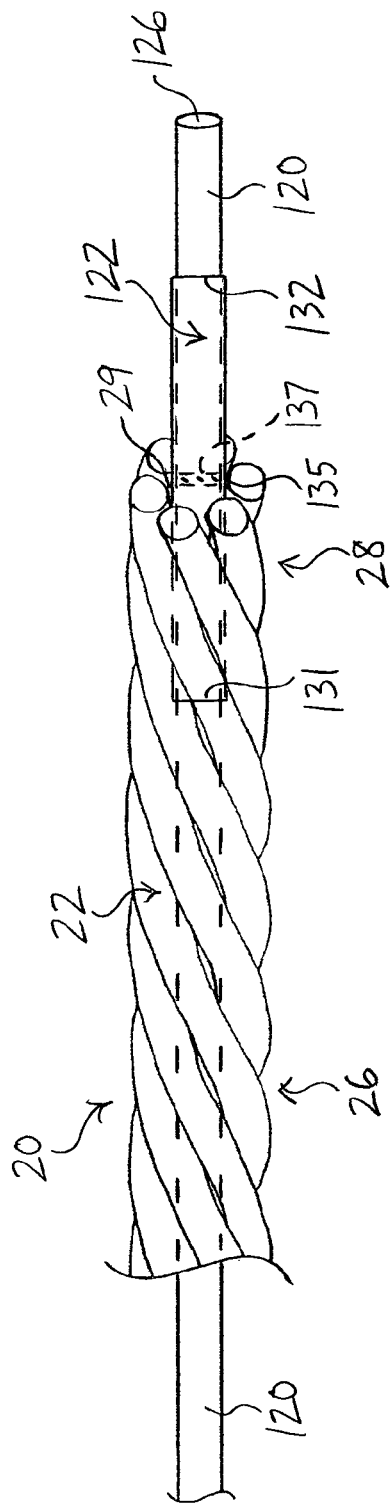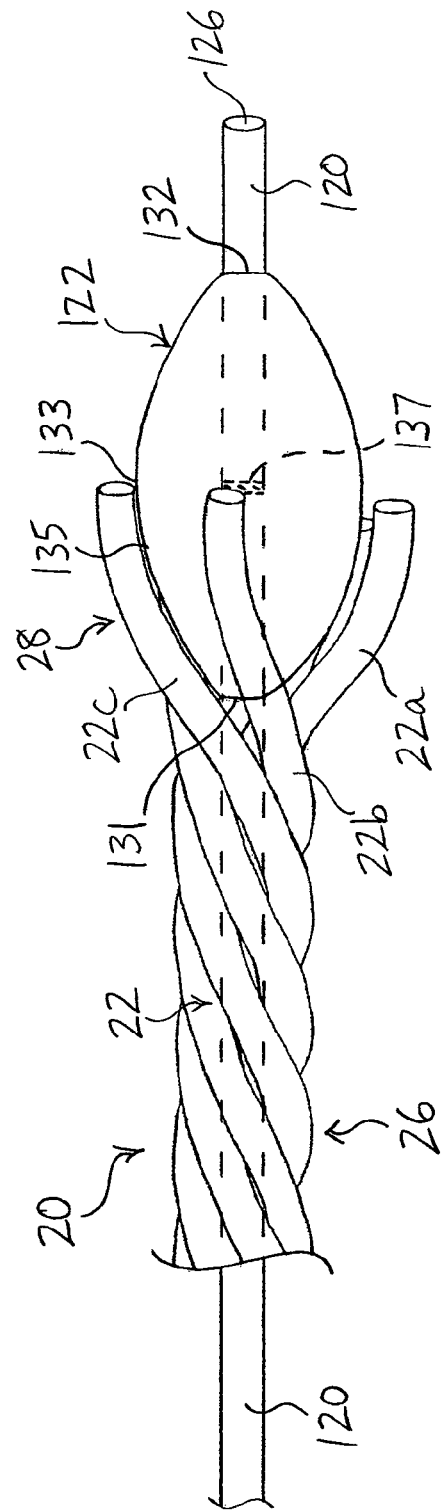
FIG. 10A
FIG. 10B

MULTI-STRANDED APPARATUS FOR TREATING A MEDICAL CONDITION

PRIORITY CLAIM

This invention claims the benefit of priority of U.S. Provisional Application Ser. No. 61/082,712, entitled "Multi-Stranded Apparatus for Treating a Medical Condition," filed Jul. 22, 2008, the disclosure of which is hereby incorporated by reference in its entirety.

BACKGROUND

The present embodiments relate generally to the field of medical devices, and more particularly, to a multi-stranded apparatus for treating a variety of medical conditions.

Various medical conditions may affect patients in an array of bodily passageways, such as vessels and ducts. One common condition is atherosclerosis, which begins with the accumulation of excess fats and cholesterol in a blood vessel. Atherosclerotic plaque forms within the walls of the vessel and may block or restrict blood flow through the vessel. The condition commonly affects the coronary arteries, the aorta, the iliofemoral arteries and the carotid arteries. Several serious consequences may result from the restricted blood flow, such as ischemic events and blood clots that may block the artery.

There are various types of athlerosclerotic plaque that may form within the vessel wall. For example, some plaque may impede flow and exhibit a calcified or fibrous nature, while other plaque may be considered "vulnerable plaque." While vulnerable plaque may develop within the arterial walls without generally narrowing the arterial lumen substantially, occlusive lesions may include calcified or fibrous plaque comprising, for example, necrotic tissue. The necrotic tissue associated with fibrous plaque may cause the arterial wall to progressively weaken, and a rupture of the intima can occur, thereby causing aneurysm and hemorrhage.

Various procedures are known for treating such occlusions in the arterial vasculature, including balloon angioplasty and stenting. During a balloon angioplasty procedure, a catheter having a deflated balloon attached thereto is inserted into a patient's vessel. Once positioned across a constricting lesion, the balloon is then inflated to widen the lumen to partially or fully restore patency to the vessel. After satisfactory widening of the stenosis has been achieved, the balloon is deflated. The catheter then is retracted and removed from the patient's vessel with the balloon in the deflated state. Stenting involves the insertion of a usually tubular member into a vessel, and may be used alone or in conjunction with an angioplasty procedure.

While conventional balloon catheters and stents are generally effective for treating occlusions and other conditions within a duct or vessel, difficulties may arise when attempting to treat or disrupt other conditions including, but not limited to, fibrous or calcified occlusions.

SUMMARY

The present invention provides apparatus suitable for treating a medical condition at a target site, such as a fibrous or hardened lesion within a vessel. In one embodiment, the apparatus comprises a plurality of strands, each having proximal and distal regions, wherein the plurality of strands are twisted in a generally helical manner to form a tubular shape. The proximal and distal regions of each of the plurality of strands comprise a contracted configuration adapted for delivery to the target site. Further, the distal region of at least one of the plurality of strands comprises an expanded, radially deployed configuration adapted to treat the medical condition. The distal region of at least one of the plurality of strands may be deployed in a self-expanding or balloon-expandable manner.

A lumen may be formed between the plurality of strands, such that the lumen is configured for the delivery of at least one medical component. In the balloon-expandable embodiment, a balloon catheter having a balloon disposed thereon may be positioned within the lumen, and the balloon may be aligned with the distal region of at least one of the plurality of strands. Inflation of the balloon is configured to radially expand at least one of the plurality of strands to facilitate treatment of the medical condition. Other instruments may be advanced through the lumen between the plurality of strands, such as embolic protection devices, stents and related deployment devices, atherectomy devices, aspiration tubing, and the like.

In one embodiment, a cross-sectional shape of at least one of the plurality of strands is circular. In an alternative embodiment, the cross-sectional shape of at least one of the plurality of strands comprises a curved inner region and a tapered outer region transitioning into a sharpened member that may be adapted to facilitate treatment of the medical condition.

In further embodiments, an attachment member may be coupled to the distal region of at least one of the plurality of strands to facilitate treatment of the medical condition. The attachment member may comprise a curved portion adapted to engage an outer surface of at least one of the plurality of strands. Further, the attachment member may comprise a sharpened outer surface, roughened surface, uneven outer surface, or other texture or shape adapted to facilitate treatment of the medical condition.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following figures and description. The components in the figures are not necessarily drawn to scale, emphasis instead being placed upon illustrating the principles of the invention. Moreover, in the figures, like referenced numerals designate corresponding parts throughout the different views.

FIG. 1 is a perspective view of a first embodiment of an apparatus for treating a medical condition, shown in a retracted state.

FIG. 2 is a perspective view of a first embodiment of an apparatus for treating a medical condition, shown in an expanded state.

FIGS. 9A-9B illustrate the apparatus of FIGS. 1-2 being deployed by retraction of a sheath in a vessel, wherein the apparatus is shown from a perspective view and the vessel is shown from a cross-sectional view for illustrative purposes.

FIGS. 10A-10B are perspective views showing the apparatus of FIGS. 1-2 being deployed by expansion of a balloon.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 3:
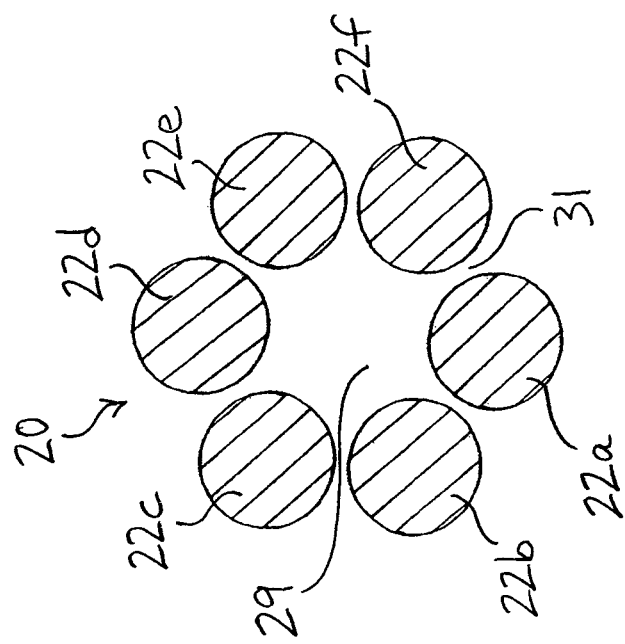
FIG. 3 is a cross-sectional view along line A-A of FIG. 1.

Referring now to FIGS. 1-3, a first embodiment of an apparatus 20 for treating a medical condition is shown. The apparatus 20 generally comprises a plurality of elongate strands 22. In the embodiments shown herein, six exemplary strands 22a-22f are shown. However, as will be explained in further detail below, any suitable number of strands 22 may be employed.

In the embodiment of FIGS. 1-3, the strands 22a-22f are twisted in a generally helical manner to form a tubular shape. A lumen 29 is formed in a central region between the strands 22a-22f, as best seen in FIG. 3. As will be explained in further detail below, various medical components may be advanced through the lumen 29 to a target site. Further, in one embodiment explained in FIGS. 10A-10B below, a balloon catheter may be disposed through the lumen 29 and used to deploy the apparatus 20.

Gaps 31 optionally may be formed between the individual strands 22a-22f when they are twisted about one another, as depicted in FIGS. 1-3. The gaps 31 may be sized to provide at least some flexibility to allow the strands 22a-22f to move with respect to one another, or alternatively, the gaps 31 may be substantially eliminated along one or more regions of the apparatus 20 to provide one or more corresponding taut regions. In effect, the interweaving of the strands 22a-22f with respect to one another may be manipulated to vary strength or flexibility characteristics along the device. Further, a sheath may be disposed over a portion of the strands 22a-22f to help keep the strands together or vary the stiffness along the device.

The apparatus 20 comprises a first, contracted delivery configuration, as shown in FIG. 1, in which it is suitable for insertion into a bodily passage, such as a duct or vessel. The apparatus 20 further comprises a second, expanded deployed configuration, shown in FIG. 2, in which a distal region of the apparatus 20 is configured to engage an interior surface of the bodily passage and/or a medical condition, such as an occlusion. The dimensions of the apparatus 20 may be tailored based on a particular surgical procedure, a particular patient's anatomy and/or other factors.

Each of the strands 22a-22f comprises a proximal region 26 and a distal region 28. At least one of the strands 22a-22f is not securely coupled to the other strands 22a-22f along its distal region 28. This allows the distal region 28 of the uncoupled strands 22a-22f to be selectively moved in a radially outward direction with respect to the other strands. In the embodiment of FIG. 2, none of the strands 22a-22f are coupled the other strands, and therefore, each of the distal regions 28 may move radially outward with respect to one another. The distal regions 28 of the strands 22a-22f may be deployed in a self-expanding or mechanically expanded manner, for example, by balloon-expansion, as generally explained below with respect to FIGS. 9-10, respectively.

In the embodiments herein, each of the distal regions 28 comprises a convex curvature 34 in the expanded deployed state, as generally depicted in FIG. 2. Alternatively, the strands 22a-22f may comprise different configurations with respect to one another in the deployed state. For example, two strands may comprise convex curvatures 34, while two strands may comprise concave curvatures, and the other two strands may comprise hook-shaped distal regions or other desired configurations. If the distal regions 28 of the strands 22a-22f comprise a self-expanding material, they may be heat-treated and configured to assume any of various expanded configurations upon retraction of a delivery sheath 100, as explained below with respect to FIGS. 9A-9B.

The distal regions 28 of the strands 22a-22f may be configured to facilitate treatment of hardened or calcified lesions in a vessel. For example, when the strands 22a-22f expand and engage a hardened or calcified lesions in a vessel, the strands may disrupt or soften the hardened or calcified lesions in a manner that may be difficult to achieve with a convention balloon catheter.

Alternatively, the distal regions 28 may be configured to facilitate other treatments in vessels or ducts, including but not limited to dilating, abrading, penetrating and cutting treatments. The distal regions 28 may comprise integrally-shaped features, such as the cross-sectional profile explained in FIG. 4 below, to facilitate treatment of a medical condition. Alternatively, as explained in FIGS. 5-8 below, one or more external attachment members may be coupled to one or more of the distal regions 28 of the strands 22a-22f to further facilitate treatment of medical conditions.

The proximal regions 26 of the strands 22a-22f may retain a constant, tubular-shaped configuration, as shown in FIGS. 1-2. In one embodiment, the proximal region 26 and the distal region 28 of each strand 22a-22f may be formed from the same material, for example, comprising shape-memory characteristics. As explained further below with respect to FIGS. 9A-9B, if a shape-memory material is employed, the apparatus 20 may be heat-treated so that the distal region 28 assumes the expanded deployed configuration shown in FIG. 2, while the proximal region 26 maintains the reduced-diameter delivery profile. Therefore, only the distal region 28 of each strand 22a-22f is configured to radially expand to treat a medical condition, as explained in FIGS. 9A-9B below.

Alternatively, each strand 22a-22f may comprise balloon-expandable characteristics. In this embodiment, a balloon, such as the balloon 122 of FIGS. 10A-10B, may be configured to expand the distal region 28 of each strand 22a-22f into engagement with a target site, as explained in further detail below.

In another embodiment, the proximal and distal regions 26 and 28 of each strand 22a-22f may comprise different characteristics. For example, the proximal region 26 may comprise a balloon-expandable material, while the distal region 28 may comprises a self-expanding material, or vice versa. If the proximal and distal regions 26 and 28 of each strand comprise different characteristics, separate portions of the strands 22a-22f may be secured together during manufacture, for example, using a spot weld, to reinforce the structural integrity of the individual strands.

In any of the above-mentioned embodiments, an external attachment means may be employed to ensure that the proximal regions 26 of each strand 22a-22f retain their constant delivery configuration shown in FIGS. 1-2. In one embodiment, the attachment means may comprise an adhesive or weld disposed in one or more of the gaps 31 along the length of the strands 22a-22f, thereby inhibiting movement of the strands 22a-22f with respect to one another along the proximal regions 26 only. Alternatively, a mechanical attachment means, such as an adhesive tape, heat-shrink tubing, one or more tie-down bands, cable-ties, and the like, may be employed to secure the configuration of the proximal regions 26.

Figure 4:
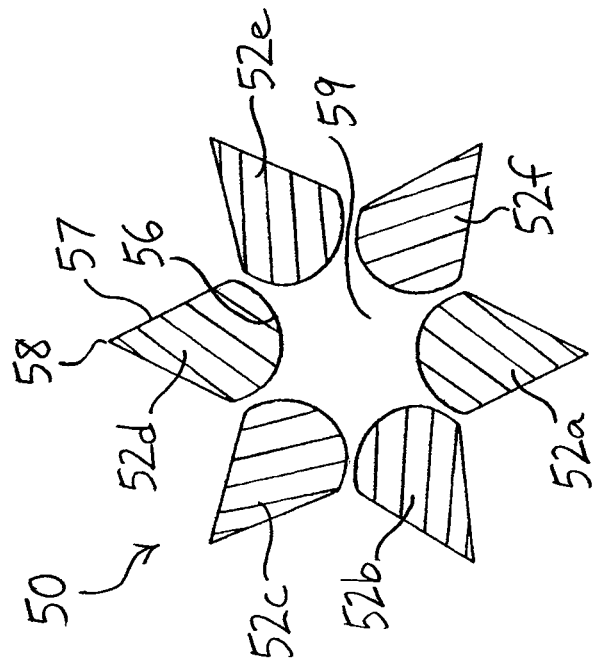
FIG. 4 is a cross-sectional view of an alternative apparatus for treating a medical condition.

Referring now to FIG. 4, in an alternative embodiment, the apparatus 50 is similar to apparatus 20 of FIGS. 1-3, with a main exception that one or more strands 52a-52f comprises a sharpened member 58. In this embodiment, each of the strands 52a-52f comprises a curved inner region 56, and a tapered outer region 57 transitioning into the sharpened member 58. A lumen 59 is formed between the plurality of curved inner regions 56, thereby providing a smooth passageway suitable for the insertion of one or more medical components.

The sharpened members 58 of the strands 52a-52f may be tailored for a particular procedure. For example, in one embodiment, the sharpened members 58 may be configured to disrupt hardened or calcified lesions formed within a vessel. As will be apparent, the strands 22a-22f may comprise other cross-sectional textures or shapes, for example, the tapers 57 may comprise different configurations and/or the sharpened members 58 may be oriented in different directions. Moreover, it is not required that each of the strands 52a-52f comprises a sharpened member, e.g., sharpened members 58 may only be provided on alternating strands 22a-22f.

In lieu of the cross-sectional shapes shown in FIGS. 3-4, the strands 22a-22f may comprise cross-sectional shapes that are square, triangular, pie-shaped, truncated cone, and the like. Moreover, while the strands 22a-22f are shown as having substantially identical cross-sectional sizes, some strands 22a-22f may comprise larger dimensions, such as cross-sectional diameters and/or tapers 57, relative to other strands 22a-22f.

Figure 5:
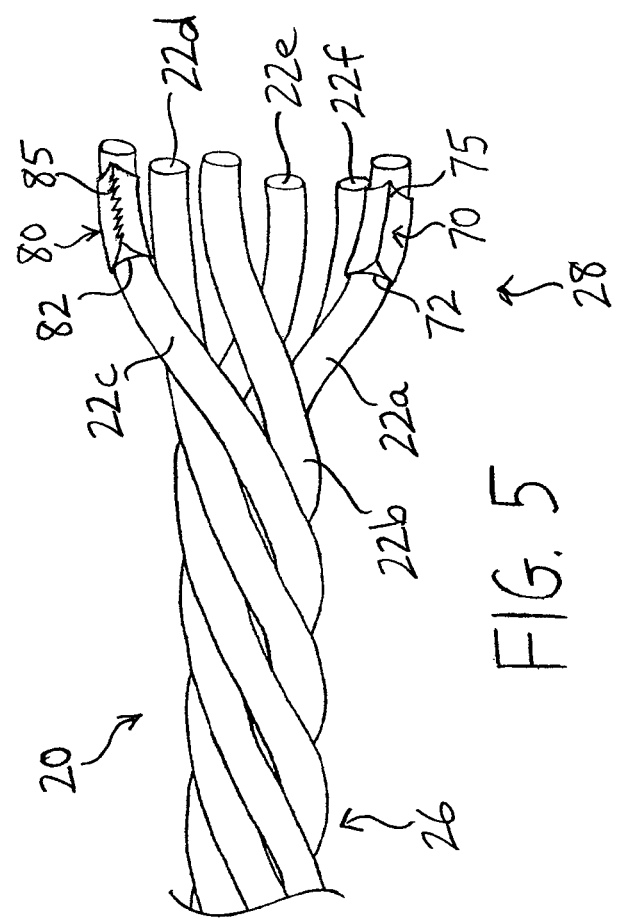
FIG. 5 is a perspective view of the apparatus of FIG. 1 having at least one attachment member.

Referring now to FIGS. 5-8, one or more attachment members may be coupled to one or more strands 22a-22f to facilitate a medical procedure, such as disruption of a hardened or calcified lesion. In FIG. 5, a first attachment member 70 has been coupled to a portion of the distal region 28 of the strand 22a, while a second attachment member 80 has been coupled to a portion of the distal region 28 of the strand 22c.

Figure 6:
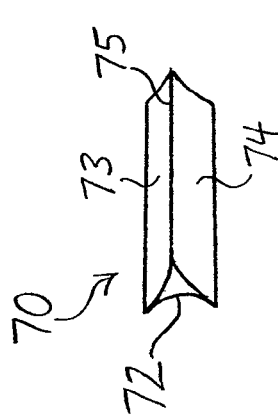
FIG. 6 is a perspective view of a first embodiment of an attachment member.

As shown in FIG. 6, the attachment member 70 may comprise a curved lower portion 72 adapted to engage an exterior surface of one of the strands 22a-22f. Preferably, the curved portion 72 matches the exterior shape of the strands 22a-22f, so that the attachment member 70 lies substantially flush with the strand, as depicted in FIG. 5. The attachment member 70 further comprises tapers 73 and 74, leading to a sharpened surface 75, as shown in FIG. 6. The sharpened surface 75 preferably is configured to facilitate treatment of a medical condition, such as a hardened or calcified lesion within a vessel.

The attachment member 70 may be coupled to the strand 22a using any suitable technique. In one example, an adhesive, such as a biocompatible glue, may be disposed on the curved portion 72 to secure the curved portion 72 to the strand 22a. Alternatively, the curved portion 72 may be aligned with the strand 22a, and then the attachment member 70 may be welded to an exterior surface of the strand 22a.

In yet a further alternative, the curved portion 72 may be crimped to the exterior surface of the strand 22a. In this example, the curved portion 72 may comprise a tubular or loop-shaped curved portion having an inner diameter slightly greater than an outer diameter of the strands 22a-22f. The loop-shaped curved portion then may be disposed over the distal end of the strand 22a and advanced in a proximal direction into the desired position along the distal region 28. Then, the loop-shaped curved portion may be manually or mechanically crimped to securely attach the curved portion 72 around the exterior surface of the strand 22a, thereby inhibiting longitudinal and rotational movement of the attachment member 70 relative to the strand 22a.

Figure 7:
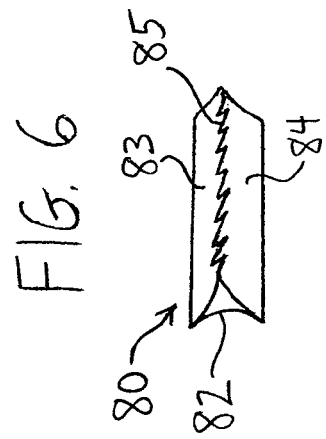
FIG. 7 is a perspective view of a second embodiment of an attachment member.

Referring to FIG. 7, an alternative attachment member 80 may comprise a curved portion 82, similar to the curved portion 72 of FIG. 6, which is adapted to engage an exterior surface of one of the strands 22a-22f. As noted above, the curved portion 82 may be coupled to the exterior surface of one or more strands 22a-22f using an adhesive, by welding, crimping, or another suitable technique. The attachment member 80 further comprises tapers 83 and 84, leading to a roughened outer surface 85, as shown in FIG. 7. The roughened outer surface 85 may comprise teeth, or another pattern or texture that preferably is suitable for facilitating treatment of a medical condition, such as a hardened or calcified lesion within a vessel.

Figure 8:
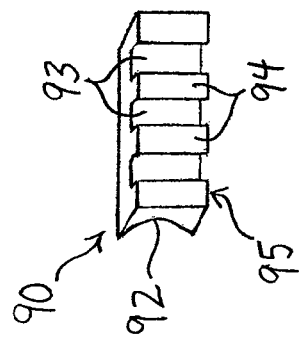
FIG. 8 is a perspective view of a third embodiment of an attachment member.

Referring to FIG. 8, a further alternative attachment member 90 may comprise a curved portion 92, similar to the curved portion 72 of FIG. 6, which is adapted to engage an exterior surface of one of the strands 22a-22f. As noted above, the curved portion 92 may be coupled to the exterior surface of one or more strands 22a-22f using an adhesive, by welding, crimping, or another suitable technique. The attachment member 90 further comprises alternating first and second tiers 93 and 94, yielding an uneven outer surface 95, as shown in FIG. 8. The uneven outer surface 95 may be particularly suitable for facilitating treatment of hardened or calcified lesions when the distal regions 28 of the strands 22a-22f are in the radially deployed configuration.

Referring now to FIGS. 9A-9B, the distal region 28 of each strand 22a-22f may comprise a shape-memory material, such as a nickel-titanium alloy (nitinol). If a shape-memory material such as nitinol is employed, the distal region 28 of each strand 22a-22f may be manufactured such that they can assume the preconfigured expanded state shown in FIG. 9B upon application of a certain cold or hot medium. More specifically, a shape-memory material may undergo a substantially reversible phase transformation that allows it to "remember" and return to a previous shape or configuration. For example, in the case of nitinol, a transformation between an austenitic phase and a martensitic phase may occur by cooling and/or heating (shape memory effect) or by isothermally applying and/or removing stress (superelastic effect). Austenite is characteristically the stronger phase and martensite is the more easily deformable phase.

In an example of the shape-memory effect, a nickel-titanium alloy having an initial configuration in the austenitic phase may be cooled below a transformation temperature ($M_f$) to the martensitic phase and then deformed to a second configuration. Upon heating to another transformation temperature ($A_f$), the material may spontaneously return to its initial, predetermined configuration, as shown in FIG. 9B. Generally, the memory effect is one-way, which means that the spontaneous change from one configuration to another occurs only upon heating. However, it is possible to obtain a two-way shape memory effect, in which a shape memory material spontaneously changes shape upon cooling as well as upon heating.

Alternatively, the distal region 28 of each strand 22a-22f may be made from other metals and alloys that are biased, such that they may be restrained by the delivery sheath 100 prior to deployment, but are inclined to return to their relaxed, expanded configuration upon deployment. Solely by way of example, the distal region 28 of each strand 22a-22f may comprise other materials such as stainless steel, cobaltchrome alloys, amorphous metals, tantalum, platinum, gold and titanium. The distal region 28 of each strand 22a-22f also may be made from non-metallic materials, such as thermoplastics and other polymers.

In use, the apparatus 20 may be loaded into a lumen 105 of the delivery sheath 100, such that the distal regions 28 of each strand 22a-22f are disposed proximal to a distal end 102 of the delivery sheath 100, as shown in FIG. 9A. A wire guide may be navigated through a patient's anatomy to a target site, such as a stenosis S within a vessel V. The apparatus 20, constrained by the delivery sheath 100, then may be advanced over the wire guide to the target site. It should be noted that the lumen 29 within the interior of the strands 22a-22f permits advancement of the apparatus 20 over the wire guide. The components may be advanced to the target site S using suitable imaging techniques, such as fluoroscopic techniques in conjunction with radiopaque bands, ultrasound techniques, and the like. If the apparatus 20 is used in the gastrointestinal tract, an endoscope having fiber optic components may be used to deliver the components through an auxiliary lumen of the endoscope.

Once the apparatus 20 is delivered and positioned, the delivery sheath 100 may be proximally retracted with respect to the apparatus 20, as shown in FIG. 9B, thereby causing the distal regions 28 of each strand 22a-22f to assume its predetermined, radially expanded configuration. As noted above, the distal region 28 of each strand 22a-22f may comprise any shape suitable for engaging, dilating, penetrating, abrading, cutting and/or otherwise treating the medical condition, such as the stenosis S, and need not necessarily assume the convex curvature depicted in FIG. 9B. It should also be noted that the proximal region 26 of each strand 22a-22f preferably does not expand radially outward upon retraction of the sheath 100, as explained above and shown in FIG. 9B.

In the expanded state, the strands 22a-22f may be manipulated to treat the medical condition, such as the stenosis S within the vessel V. For example, in the case of a hardened or fibrous lesion in a vessel, the distal regions 28 of the strands 22a-22f may be rotated and/or advanced longitudinally with respect to the stenosis S. A handle may be coupled to the proximal region 26 of the strands 22a-22f to impart the desired rotational and/or longitudinal motion, thereby facilitating treatment of the stenosis S. Moreover, one or more of the distal regions 28 may comprise an imaging element, such as a crimped radiopaque marker, to facilitate visualization and orientation of the apparatus 20 during treatment.

If desired, the wire guide used to deliver the apparatus 20 may be removed from within the lumen 29 of the strands 22a-22f. Subsequently, one or more medical components may be inserted through the lumen 29 and advanced distally towards the target site within the vessel V. Solely by way of example, an embolic protection device, balloon catheter, atherectomy device, aspiration tubing, stent and related deployment mechanisms and/or other devices may be advanced through the lumen 29 of the apparatus 20 and used in conjunction with the apparatus 20 at the treatment site.

Once the procedure is completed, the delivery sheath 100 may be advanced distally with respect to the strands 22a-22f, thereby causing the distal end 102 of the delivery sheath to cover each of the strands 22a-22f and retain the strands 22a-22f in the retracted state shown in FIG. 9A. The apparatus 20 then may be removed from a patient's body.

Referring now to FIGS. 10A-10B, a portion of the apparatus 20 may be expanded by a balloon catheter 120 having a balloon 122 disposed thereon. The catheter 22 may comprise a flexible, tubular member that may be formed from one or more semi-rigid polymers. For example, the catheter may be manufactured from polyurethane, polyethylene, tetrafluoroethylene, polytetrafluoroethylene, fluorinated ethylene propylene, nylon, PEBAX or the like. The balloon 122 may be manufactured from a balloon material, e.g., PEBAX, nylon, Hytrel, Arnitel or other polymers, that is suitable for use during an interventional procedure.

In this embodiment, the balloon catheter 120 has a working lumen 126, in addition to an inflation lumen (not shown) in communication with an interior surface of the balloon 122. The apparatus 20 may be advanced to a target site using a wire guide, and may be positioned using suitable imaging techniques, as described above. An outer sheath, such as the delivery sheath 100 of FIGS. 9A-9B, may be used to cover the apparatus 20 during delivery. The balloon catheter 120 may be advanced through the lumen 29 of the apparatus 20, via the wire guide, such that a portion of the balloon 122 is aligned with a portion of the distal region 28 of the strands 22a-22f. The balloon catheter 120 may comprise at least one imaging marker 137, which may be visualized using known techniques, and may be employed to facilitate alignment of the balloon 122.

In FIG. 10B, the balloon 122 then is expanded, via the inflation lumen, to expand the distal region 28 of each strand 22a-22f into engagement with a target site. Advantageously, the distal region 28 of each strand 22a-22f may engage a portion of the target site, and provide a force different from the force provided solely by expansion of the balloon 122. The balloon 122 may remain inflated, while the distal regions 28 of the strands 22a-22f may be rotated and/or advanced longitudinally with respect to the lesion, for example, to facilitate treatment of a hardened or fibrous lesion in a vessel. As in the embodiment of FIGS. 9A-9B, one or more other medical components, such as an embolic protection device, atherectomy device, aspiration tubing, or stent and related deployment mechanisms, may be inserted through the lumen 29 and advanced distally towards the target site, either before or after use of the balloon catheter 120. Once the procedure is completed, an outer sheath, such as the delivery sheath 100 of FIGS. 9A-9B, may be advanced distally with respect to the strands 22a-22f to restrain the strands 22a-22f for removal of the apparatus 20 from the patient's body.

In the embodiment of FIG. 10B, the balloon 122 comprises an elliptical shape having proximal and distal ends 131 and 132, respectively, and a central region 133 disposed therebetween. A curved region 135 is formed between the proximal end 131 and the central region 133, as shown in FIG. 10B. The curved region 135 may be configured to match the desired shape of the strands 22a-22f in the expanded deployed configuration, as depicted in FIG. 10B. In this embodiment, the imaging marker 137 may be substantially aligned with the central region 133 of the balloon 122, to facilitate alignment of the central region 133 with a distal end of the strands 22a-22f.

It should be noted that while six total strands 22a-22f are depicted herein, greater or fewer strands may be employed. Moreover, the strands 22a-22f may comprise any shape suitable for engaging, dilating, penetrating, abrading, cutting and/or otherwise treating tissue, and need not necessarily assume the expanded shape depicted herein. Further, while use of the apparatus 20 has been explained primarily with respect to treatment of hardened or fibrous lesions in a vessel, it will be apparent that apparatus 20 may be useful in several other medical procedures in an array of bodily passageways.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. Apparatus suitable for treating a medical condition at a target site, the apparatus comprising:
   a plurality of strands, each having proximal and distal regions, wherein the plurality of strands are twisted in a generally helical manner to form a tubular shape having a longitudinal axis;
   wherein the proximal and distal regions of each of the plurality of strands comprise a contracted configuration adapted for delivery to the target site; and
   wherein the distal region of at least one of the plurality of strands is uncoupled to the distal regions of the other strands, thereby allowing the distal region of the uncoupled strand to be selectively moved in a radially outward direction relative to the other strands to facilitate treatment of the medical condition,
   wherein the cross-sectional shape of at least one of the plurality of strands comprises a curved inner region and a tapered outer region transitioning into a sharpened member, wherein the sharpened member is adapted to facilitate treatment of the medical condition.

2. The apparatus of claim 1 wherein none of the distal regions of the plurality of strands are coupled together, thereby allowing each of the distal regions of the plurality of strands to move radially outward with respect to one another.

3. The apparatus of claim 1 further comprising a lumen formed within the plurality of strands and along the longitudinal axis, wherein the lumen is configured for the delivery of at least one medical component.

4. The apparatus of claim 1 wherein the movable distal region of the strand is configured to be self-expandable and biased towards the deployed configuration.

5. The apparatus of claim 1 wherein the movable distal region of the strand is configured to be balloon-expanded into the deployed configuration.

6. The apparatus of claim 1 wherein the cross-sectional shape of at least one of the plurality of strands is circular.

7. The apparatus of claim 1 further comprising an attachment member coupled to at least one of the plurality of strands, wherein the attachment member is adapted to facilitate treatment of the medical condition.

8. The apparatus of claim 7 wherein the attachment member comprises a curved lower portion adapted to engage a curved outer surface of at least one of the plurality of strands in a substantially flush manner.

9. The apparatus of claim 7 wherein the attachment member comprises a sharpened outer surface adapted to facilitate treatment of the medical condition.

10. Apparatus suitable for treating a medical condition at a target site, the apparatus comprising:
    a plurality of strands, each having proximal and distal regions, wherein the plurality of strands are twisted in a generally helical manner to form a tubular shape having a longitudinal axis;
    wherein the proximal and distal regions of each of the plurality of strands comprise a contracted configuration adapted for delivery to the target site,
    wherein the distal region of at least one of the plurality of strands is uncoupled to the distal regions of the other strands, thereby allowing the distal region of the uncoupled strand to be selectively moved in a radially outward direction relative to the other strands to facilitate treatment of the medical condition; and
    an attachment member coupled to at least one of the plurality of strands, wherein the attachment member is adapted to facilitate treatment of the medical condition,
    wherein the attachment member comprises a curved lower portion adapted to engage a curved outer surface of at least one of the plurality of strands in a substantially flush manner.

11. The apparatus of claim 10 wherein none of the distal regions of the plurality of strands are coupled together, thereby allowing each of the distal regions of the plurality of strands to move radially outward with respect to one another.

12. The apparatus of claim 10 further comprising a lumen formed within the plurality of strands and along the longitudinal axis, wherein the lumen is configured for the delivery of at least one medical component.

13. The apparatus of claim 10 wherein the movable distal region of the strand is configured to be self-expandable and biased towards the deployed configuration.

14. The apparatus of claim 10 wherein the movable distal region of the strand is configured to be balloon-expanded into the deployed configuration.

15. Apparatus suitable for treating a medical condition at a target site, the apparatus comprising:
    a plurality of strands, each having proximal and distal regions, wherein the plurality of strands are twisted in a generally helical manner to form a tubular shape having a longitudinal axis;
    wherein the proximal and distal regions of each of the plurality of strands comprise a contracted configuration adapted for delivery to the target site,
    wherein the distal region of at least one of the plurality of strands is uncoupled to the distal regions of the other strands, thereby allowing the distal region of the uncoupled strand to be selectively moved in a radially outward direction relative to the other strands to facilitate treatment of the medical condition; and
    an attachment member coupled to at least one of the plurality of strands, wherein the attachment member is adapted to facilitate treatment of the medical condition,
    wherein the attachment member comprises a sharpened outer surface adapted to facilitate treatment of the medical condition.

16. The apparatus of claim 15 wherein none of the distal regions of the plurality of strands are coupled together, thereby allowing each of the distal regions of the plurality of strands to move radially outward with respect to one another.

17. The apparatus of claim 15 further comprising a lumen formed within the plurality of strands and along the longitudinal axis, wherein the lumen is configured for the delivery of at least one medical component.

18. The apparatus of claim 15 wherein the movable distal region of the strand is configured to be self-expandable and biased towards the deployed configuration.

19. The apparatus of claim 15 wherein the movable distal region of the strand is configured to be balloon-expanded into the deployed configuration.

20. The apparatus of claim 15 wherein the cross-sectional shape of at least one of the plurality of strands is circular.

* * * * *